United States Patent

Ross et al.

[11] Patent Number: 5,807,314
[45] Date of Patent: Sep. 15, 1998

[54] FEEDING TUBE AND METHOD FOR PLACING SAME

[75] Inventors: Jeffrey R. Ross; Kathleen Rowland, both of Dublin, Ohio

[73] Assignee: Abbott Laboratories, Abbott Park, Ill.

[21] Appl. No.: 729,605

[22] Filed: Oct. 11, 1996

[51] Int. Cl.$^6$ .................................................. A61M 31/00
[52] U.S. Cl. .............................. 604/49; 604/53; 604/264; 604/54; 604/270
[58] Field of Search ................................. 604/49, 50–53, 604/264, 280, 270, 54

[56] References Cited

U.S. PATENT DOCUMENTS

| | | | |
|---|---|---|---|
| 4,762,519 | 8/1988 | Frimberger | 604/280 |
| 5,037,387 | 8/1991 | Quinn et al. | 604/51 |
| 5,098,378 | 3/1992 | Pionted et al. | 604/49 |
| 5,112,310 | 5/1992 | Grobe | 604/175 |
| 5,318,530 | 6/1994 | Nelson, Jr. | 604/54 |

OTHER PUBLICATIONS

K.G. Sylvester, D.L. Paskin, A.L. Schuricht, "Combined Laparoscopic–Endoscopic Gastrostomy," Surgical Endoscopy (1994) 8:1072–1075.

*Primary Examiner*—Wynn Wood Coggins
*Assistant Examiner*—Deborah Blyveis
*Attorney, Agent, or Firm*—Brian R. Woodworth

[57] ABSTRACT

An apparatus for placing a feeding tube in a patient. The apparatus includes an introducer section defining a lumen therethrough and a tube section defining a lumen therethrough. A proximal end portion of the introducer section is mounted on a distal end portion of tube section such that the respective lumen are in fluid communication. Apertures are formed at the distal end of the introducer section and at the proximal portion of the tube section. The respective lumen are constructed to receive therein an endoscope. A graspable member is mounted on the distal end portion of the introducer section. A retaining member is mounted on the proximal end portion of the tube section. In order to place the apparatus in a patient, an endoscope is inserted into the aperture defined through the tube section and advanced such that a viewing portion of the endoscope is positioned proximal to the aperture defined through the distal end portion of the introducer section. The distal end portion of the introducer section is introduced into the patient's mouth and advanced through the patient's esophagus and into the patient's stomach. An incision is made through the patient's abdominal wall and into the patient's stomach. A grasping tool is inserted through the incision and is used to grasp the graspable member. The grasping tool and the apparatus are drawn through the incision until the retaining member engages the stomach. The endoscope remains in the patient's stomach as the apparatus of the present invention is drawn outwardly through the abdominal incision. The endoscope is then withdrawn from the patient's stomach through the patient's mouth.

8 Claims, 3 Drawing Sheets

FEEDING TUBE AND METHOD FOR PLACING SAME

TECHNICAL FIELD

This invention relates to an improved feeding tube for the delivery of nutritional products to the gastrointestinal tract of a patient and a method for placing such a feeding tube. In particular, the apparatus and method of the present invention are designed to reduce trauma to the patient and the time required for placement of the tube by reducing the number of times that instruments must be passed through the esophagus of the patient.

BACKGROUND OF THE INVENTION

Gastrostomy and jejunostomy tubes are used to deliver nutritional products to the gastrointestinal tract of a patient. Gastrostomy tubes are positioned such that a nutritional product is delivered percutaneously from an external source directly to the patient's stomach. Jejunostomy tubes are positioned such that the nutritional product is delivered to the patient's small bowel. Gastrostomy and jejunostomy tubes are referred to collectively herein as "feeding tubes."

The first step in placing a feeding tube in a patient typically involves the passing of an endoscope down the patient's esophagus in order to view the esophagus and to ensure that there are no obstructions or lesions in the esophagus that will inhibit or preclude the passage of the feeding tube through the esophagus. The endoscope also is used to examine the interior of the stomach and/or the small bowel. Next, the doctor selects the site through which the feeding tube will be introduced and transilluminates the selected site by directing light outwardly from endoscope such that the light shines through the patient's abdominal wall, thereby allowing the doctor to identify the entry site from a point outside of the patient's body. The doctor then makes an incision through the abdominal wall into the stomach and passes a first end of a wire percutaneously into the stomach. The first end of the wire is grasped by a grasping tool associated with the endoscope, and the endoscope and the wire are drawn outwardly from the patient's stomach and esophagus and through the patient's mouth. Upon completing this step of the procedure, a second end of the wire remains external to the patient's abdominal wall while the first end of the wire extends outwardly through the patient's mouth.

In one technique for feeding tube placement, the first end of the wire is attached to a feeding tube. By pulling on the second end of the wire, the feeding tube is pulled through the patient's mouth and esophagus, and then into stomach. Further pulling of the second end of the wire causes the feeding tube to exit the stomach through the incision in the abdominal wall. The feeding tube is pulled through the incision until a retaining member mounted on the second end of the feeding tube engages the interior of the stomach. This technique is referred to as a "pull" technique.

In an alternative technique for feeding tube placement, the feeding tube is placed over the wire and is pushed along the wire such that the feeding tube passes through the patient's mouth, esophagus, and stomach until the first end of the feeding tube exits through the incision in the abdominal wall. The feeding tube is then drawn through the abdominal incision until the retaining member on the second end of the feeding tube engages the interior of the stomach. This technique is referred to as a "push" technique.

Feeding tubes used with push and pull placement techniques define a feeding lumen therethrough. The feeding lumen is open to an external environment of the feeding tube at the second end of the tube, i.e., at the end of the tube proximal the retaining member. The first end of the feeding tubes placed using the push technique is closed and preferably has a substantially conical shape in order to act as a dilator as the first end of the feeding tube is drawn through the incision. Thus, the feeding lumen of tubes placed using the pull technique is not open to an external environment of the feeding tube at the first end of the feeding tube.

Following placement of the feeding tube using either the push or the pull technique, the doctor again inserts the endoscope through the patient's mouth and esophagus in order to determine the orientation of the retaining member and tube within the stomach.

In order to minimize the time required for placement of the gastrostomy or jejunostomy tube, and more importantly in order to minimize the trauma to the patient associated with placement of the tube, it is desirable to employ a feeding tube placement technique that reduces the number of times that devices must be passed through the patient's esophagus, either into or from the stomach. As above-discussed, the push and pull techniques require at least five (5) separate one-way passes through the esophagus, four (4) of which are attributable in whole or in part to scoping the patient prior to and following placement of the tube. The apparatus and method of the present invention reduce the number of passes required for the proper placement of a feeding tube, thereby reducing trauma to the patient and reducing the time required to complete the placement procedure.

SUMMARY OF THE INVENTION

The present invention is directed to an apparatus and method for the placement of gastrostomy and jejunostomy tubes. In a first embodiment of the apparatus of the present invention, the apparatus includes an introducer section defining a lumen therethrough. The introducer section includes a distal end portion and a proximal end portion, the lumen being open to an external environment of the introducer section through an aperture formed through the distal end portion thereof. A graspable member is mounted on the distal end portion of the introducer section.

The apparatus of the first embodiment of the present invention further includes a tube section defining a lumen therethrough. The tube section includes a distal end portion and a proximal end portion, the lumen being open to an external environment of the tube section through an aperture formed through the proximal end portion thereof. The distal end portion of the tube section is connected to the proximal end portion of the introducer section such that the respective lumen of the introducer section and the tube section are in fluid communication. A retaining member is mounted on the proximal end portion of the tube section.

The first embodiment of the method of the present invention includes the step of providing an apparatus having an introducer section and a tube section in accordance with the apparatus of the first embodiment of the present invention. An endoscope also is provided and is placed within the lumen defined by the introducer section and the tube section such that a viewing portion of the endoscope is positioned proximal to the aperture formed through the distal end portion of the introducer section, whereby the endoscope can receive and transmit images of an external environment of the distal end portion of the introducer section as the feeding tube and the endoscope are advanced into the gastrointestinal tract.

The apparatus of the present invention, with the endoscope disposed therein, is introduced into the patient's mouth and is advanced into the patient's stomach by pushing the apparatus. An incision is then formed through the patient's abdominal wall into the stomach. A cannula is inserted through the incision and into the patient's stomach and a grasping device is introduced through the cannula and into the patient's stomach. The graspable member of the apparatus of the present invention is grasped using the grasping device and the distal end portion of the introducer section is drawn outwardly through the abdominal incision until the retaining member on the tube section engages the interior of the stomach. Concurrently, the endoscope is restrained from moving with the feeding tube such that the feeding tube passes over the endoscope, thereby leaving the endoscope in the patient's stomach. The endoscope is then removed from the body of the patient.

In a second embodiment of the apparatus of the present invention, the apparatus includes an introducer section having a distal end portion and a proximal end portion. The introducer section has a length of at least approximately 12 inches and is constructed of a material having a Shore A hardness value of substantially 60–90. A graspable member is mounted on the distal end portion of the introducer section.

The apparatus of the second embodiment of the present invention further includes a tube section defining a lumen therethrough. The tube section includes a distal end portion and a proximal end portion, the lumen being open to an external environment of the tube section through an aperture formed through the proximal end portion thereof. The distal end portion of the tube section is connected to the proximal end portion of the introducer portion. A retaining member is mounted on the proximal end portion of the tube section.

The second embodiment of the method of the present invention includes the step of providing an apparatus having an introducer section and a tube section in accordance with the apparatus of the second embodiment of the present invention. The apparatus of the second embodiment of the present invention is introduced into the patient's mouth and is advanced into the patient's stomach. An incision is formed through the patient's abdominal wall into the stomach and a cannula is inserted therethrough. A grasping device is introduced through the cannula and into the stomach. The graspable member of the apparatus is grasped using the grasping device and the distal end portion of the introducer section is drawn outwardly through the abdominal incision until the retaining member on the tube section engages the interior of the stomach.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENT

While this invention is susceptible of embodiment in many different forms, this specification and the accompanying drawings disclose only one specific form as an example of the invention. The invention is not intended to be limited to the embodiment so described. The scope of the invention is pointed out in the appended claims.

The figures illustrating the apparatus show some elements that are known and that will be recognized by one skilled in the art. The detailed descriptions of such elements are not necessary to an understanding of the invention, and accordingly, are herein presented only to the degree necessary to facilitate an understanding of the novel features of the present invention.

The apparatus of this invention is used with certain conventional components the details of which, although not fully illustrated or described, will be apparent to those having skill in the art and an understanding of the necessary functions of such components.

Figure 1:
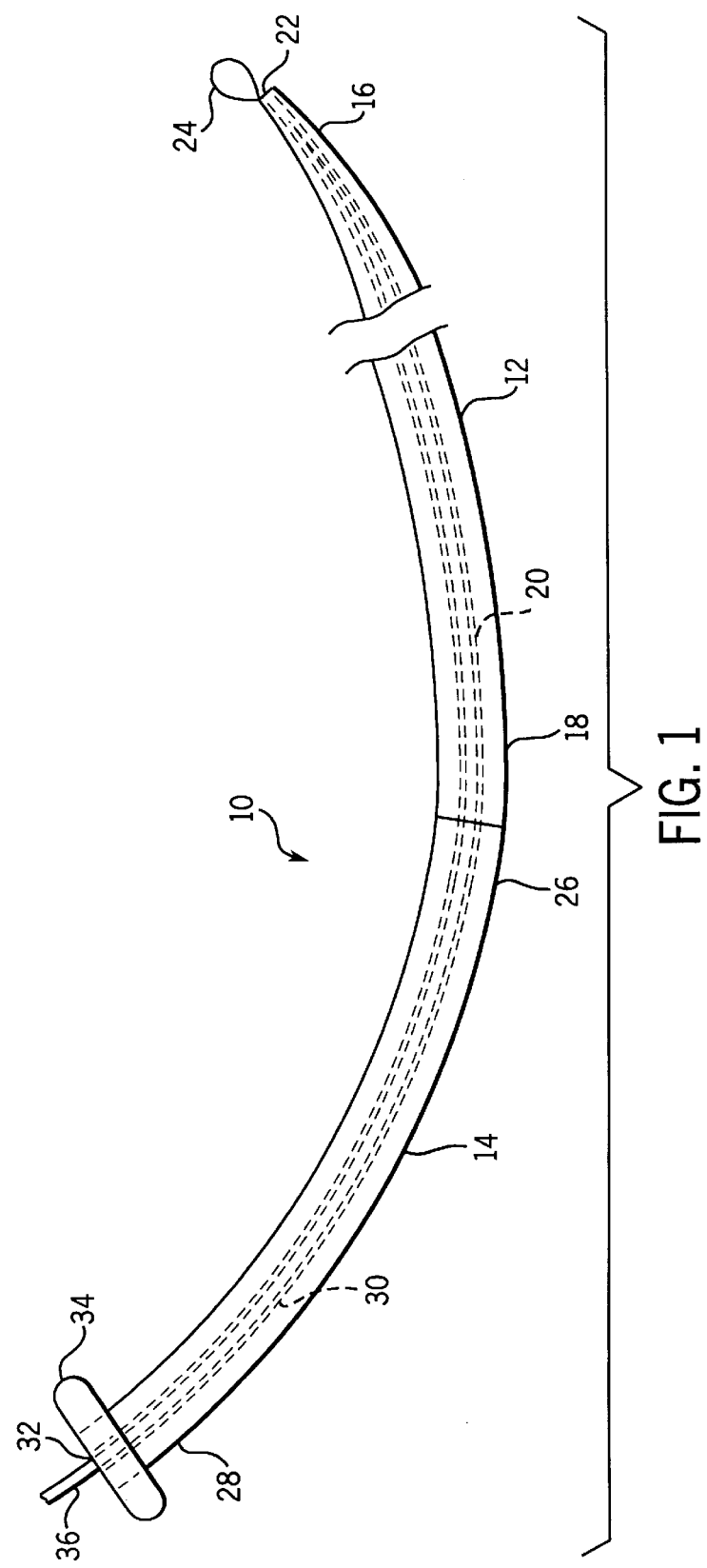
FIG. 1 is a plan view of an apparatus constructed in accordance with a first embodiment of the present invention.

An apparatus constructed in accordance with a first embodiment the present invention is generally indicated at 10 in FIG. 1. Apparatus 10 is constructed of biocompatible materials and includes an introducer section 12 and a tube section 14. Introducer section 12 includes distal end portion 16 and proximal end portion 18. Introducer section 12 defines lumen 20 therethrough, as depicted by hidden lines in FIG. 1. Although introducer section 12 is depicted herein as being substantially annular in cross-section, it will be appreciated that introducer section 12 and lumen 20 formed thereby can have a variety of other configurations, e.g., polygonal, without departing from the scope of the present invention. Lumen 20 terminates at aperture 22 defined through distal end portion 16 of introducer section 12 and, in the preferred embodiment of the present invention, is in fluid communication with an external environment of introducer section 12 through aperture 22.

Figure 2:
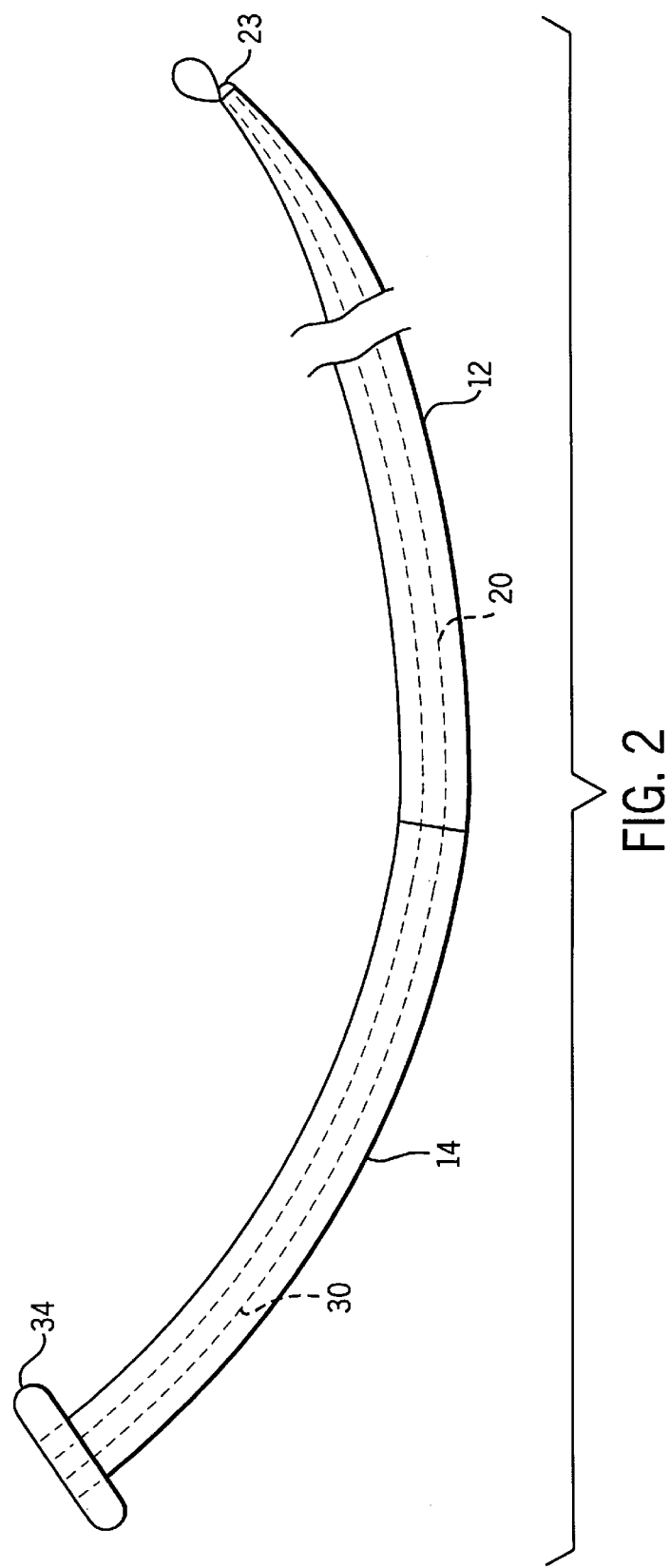
FIG. 2 is a plan view of an apparatus constructed in accordance with a second embodiment of the present invention.
Figure 3:
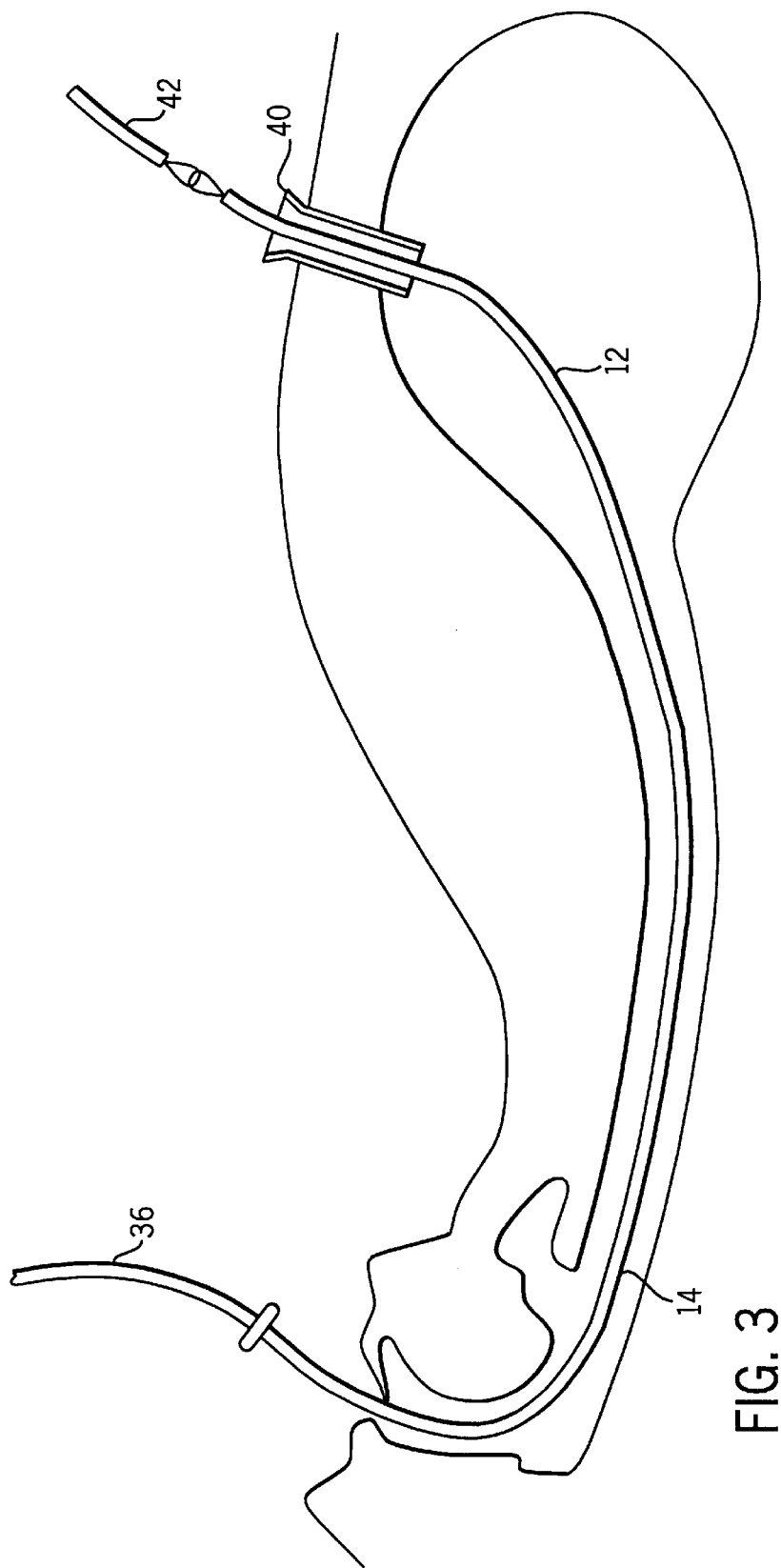
FIG. 3 is a plan view depicting an apparatus in accordance with the present invention being placed in a patient in accordance with a method of the present invention.

In the preferred embodiment of the present invention depicted in FIG. 1, aperture 22 is uncovered such that lumen 20 is in fluid communication with an external environment of distal end portion 16 of introducer section 12 through aperture 22. However, aperture 22 can be covered by closure 23 as depicted in FIG. 2. Closure 23 preferably is constructed of a known biocompatible material that will allow an endoscope positioned within lumen 20 at distal end portion 16 to receive an image of the external environment of introducer section 12, i.e., a substantially transparent material. For example, closure 23 can be a lens of known configuration, e.g., convex, concave, or plano, that is constructed of a biocompatible material. In the event that closure 23 is present, it may be preferable to provide an alternative aperture through introducer section 12 in order to allow insufflation of the stomach therethrough.

In the first embodiment of the present invention depicted in FIG. 1, introducer section 12 has a length sufficient to reach from the mouth to the stomach of a patient. In this way, introducer section 12 can be used to push distal end portion 16 thereof into the patient's stomach. For this reason, introducer section 12 preferably has a length of at least approximately 12 inches. In a preferred embodiment of the present invention, introducer section 12 has a length in the range of approximately 12 to approximately 30 inches. One of ordinary skill in the art will appreciate that shorter lengths are appropriate where apparatus 10 is designed to be used with children.

Graspable member 24 is mounted on distal end portion 16 of introducer section 12. In the first and second embodiments of the present invention depicted in FIGS. 1 and 2, graspable member 24 is a loop of biocompatible material, e.g., a suture material. However, it will be appreciated that a variety of configurations of graspable member 24 are possible without departing from the spirit and scope of the present invention as claimed in the appended claims. For example, graspable member 24 can be constructed in the form of a tab or flap extending from distal end portion 16 of introducer section 12. As discussed in detail herein with respect to the method of the present invention, graspable member 24 is constructed to be grasped by a grasping tool inserted into the stomach through a cannula positioned through patient's abdominal wall. Graspable member 24 also is constructed such that introducer section 12 can be drawn outwardly through the abdominal incision by the grasping tool without graspable member 24 breaking from introducer section 12.

Tube section 14 of the present invention includes distal end portion 26 and proximal end portion 28. Tube section 14 defines lumen 30 therethrough, as depicted by hidden lines in FIG. 1. Although tube section 14 is depicted herein as being substantially annular in crosssection, it will be appreciated that tube section 14 and lumen 30 formed thereby can have a variety of other configurations, e.g., D-shaped or polygonal, without departing from the scope of the present invention.

In both the first and second embodiments of apparatus 10 of the present invention, distal end portion 26 of tube portion 14 is mounted on proximal end portion 18 of introducer section 12. Tube section 14 is mounted on introducer section 12 such that lumen 20 is in fluid communication with lumen 30. In the preferred configuration of the present invention, lumen 20 and lumen 30 are substantially coaxial and define a substantially continuous lumen through apparatus 10. Introducer section 12 and tube section 14 are mounted by known mechanical or adhesive techniques. Alternatively, introducer section 12 and tube section 14 can be integrally formed. All such methods for connecting introducer section 12 and tube section 14 are included within the scope of the term "mounted on" for the purposes of this disclosure.

Lumen 30 terminates at aperture 32 defined through proximal end portion 28 of tube section 14. Aperture 32 provides communication between lumen 30 and an external environment of proximal end portion 28 of tube section 14. In the preferred configuration of the first embodiment of the present invention, aperture 32 is configured to permit an endoscope to be inserted into lumen 30 of tube section 14 through aperture 32.

Retaining member 34 is mounted on proximal end portion 28 of tube section 14. Retaining member 34 is constructed to preclude premature removal of proximal end portion 28 of tube section 14 from the stomach of a patient through an abdominal incision or stoma. One of ordinary skill will appreciate that retaining member 34 can have a variety of known configurations, including inflatable balloons, preformed balloons, foamfilled balloons, collapsible structures, and non-collapsible structures without departing from the scope of the present invention. Retaining member 34 can be positioned adjacent to or proximal to terminal end 29 of proximal end portion 28 of tube section 14 when apparatus 10 is used as a gastrostomy tube, or retaining member 34 can be spaced from terminal end 29 of proximal end portion 28 of tube section 14. The location and configuration of retaining member 34 will be selected by the doctor based upon the patient's needs and the doctor's preferences.

One of ordinary skill in the art will recognize that tube section 14 of the first and second embodiments of present invention is a percutaneous endoscopic gastrostomy ("PEG") device. Tube section 14 can be configured in accordance with the teachings of a variety of known PEG devices. For example, tube section 14 can further include an inflation lumen in fluid communication with retaining member 34 where retaining member 34 is an inflatable balloon.

In the embodiments of the present invention depicted in FIGS. 1 and 2, the outside diameter of distal end portion 16 of introducer section 12 is smaller than outside diameter of tube portion 14. Due to the reduced diameter of distal end portion 16 of introducer section 12, introducer section 12 will pass more easily through an abdominal incision. In the preferred embodiment of the present invention, distal end portion 16 of introducer section 12 is substantially conical in shape such that the outside diameter increases from distal end portion 16 to proximal end portion 18. Thus, distal end portion 16 of introducer section 12 acts as a dilator as it passes through an abdominal incision, thereby facilitating the passage of tube section 14 through the abdominal incision. The outside dimension of tube section 14 preferably is substantially the same as the outside dimensions of known PEG tubes, i.e., approximately 12–24 French.

Introducer section 12 of the second embodiment of the present invention depicted in FIG. 2 preferably is constructed of a material having a rigidity sufficient to permit introducer section 12 to be advanced down the esophagus of the patient by pushing introducer section 12. For example, introducer section 12 of the second embodiment of the present invention can be constructed of a polyurethane material such as those used in nasogastric tubes. Such polyurethane materials typically have Shore A hardness values in the range of substantially 60–90. However, it will be appreciated that endoscope 36, when inserted into introducer section 12 and tube section 14 of the first embodiment of the apparatus of the present invention, will add rigidity to introducer section 12, particularly when endoscope 36 is constructed of a relatively rigid material. Thus, introducer section 12 may also be constructed of softer polyurethane materials, silicone materials, and other biocompatible materials.

Tube section 14 can be constructed of the same material as introducer section 12, but preferably is constructed of a relatively soft material such as silicone rubber or polyurethane having a Shore A hardness value in the range of substantially 30–70, although tube section 14 can have a greater Shore A hardness value.

The present invention further includes a method for placing a PEG tube in a patient. The first embodiment of the method of the present invention includes the step of providing an apparatus constructed in accordance with the first embodiment of the present invention. An endoscope 36 also is provided. Endoscope 36 is inserted into aperture 32 defined through proximal end portion 28 of tube section 14 and is advanced through tube section 14 and introducer section 12 such that viewing portion 38 of endoscope 36 is positioned within distal end portion 16 of introducer section 12. Viewing portion 38 of endoscope 36 preferably is positioned such that it will provide a view through aperture 22 of the esophagus and stomach of the patient as distal end portion 16 of introducer section 12 is advanced therethrough. It will be appreciated that endoscope 36 can be pre-placed within apparatus 10.

Distal end portion 16 of introducer section 12 having viewing portion 38 of endoscope 36 disposed therein is inserted into the mouth of the patient and is advanced into the stomach of the patient by pushing on introducer section 12. As introducer section 12 is advanced into the esophagus and stomach of the patient, a medical professional observes the condition of the esophagus and stomach using endoscope 36 in order to identify any lesions or other obstructions that may impede or preclude placement of apparatus 10 in the patient. If desired, introducer section 12 can be advanced into the patient's small bowel, thereby enabling the medical professional to observe the condition of the small bowel. If introducer section 12 is advanced into the small bowel, it must be removed to the stomach prior to proceeding with the method of the present invention.

An appropriate site for placement of the apparatus of the present invention is selected by the doctor while viewing the interior of the stomach through endoscope 36. The doctor typically will select the target site in order to avoid lesions and blood vessels in the stomach. Upon selection of an appropriate site, endoscope 36 can be used to transilluminate the stomach, thereby providing a visual, external indication of the position of the target site. A topical anesthetic such as lidocaine is then applied to the selected site on the patient's skin and an incision is made through the patient's abdominal wall and into the stomach using known surgical tools. Needle or cannula 40 defining a channel therethrough is inserted into the incision and is advanced into the patient's stomach to provide a channel from a point external to the patient to the interior of the stomach.

Grasping tool 42 is inserted through needle 40 and into the patient's stomach and is manipulated so that it can grasp graspable member 24. This procedure is facilitated by viewing the respective positions of graspable member 24 and grasping tool 42 using endoscope 36. Grasping tool 42 can be a variety of known medical tools used to grasp a structural element, including forceps, hooks, and snares. However, it will be appreciated that grasping tool 42 must be small enough to fit through needle 40.

Once grasping tool 42 has grasped graspable member 24, grasping tool 42 is pulled outwardly through the abdominal incision, thereby causing distal end portion 16 of introducer section 12 to pass outwardly through the abdominal incision. Endoscope 36 preferably is held substantially stationary by the medical professional as grasping tool 42 is pulled outwardly, thereby causing introducer section 12 and tube section 14 to pass over endoscope 36. This is accomplished by holding endoscope 36 at a position external to the patient's mouth. Further outward movement of grasping tool 42 and introducer section 12 is imparted until retaining member 34 of tube section 14 engages the interior wall of the patient's stomach. At this point, endoscope 36 preferably is positioned within the patient's stomach but is no longer surrounded by introducer section 12 or tube section 14 of apparatus 10. If for some reason endoscope 36 is still positioned within tube section 14, e.g., endoscope 36 was inadvertently displaced relative to tube section 14 during insertion into the stomach, endoscope 36 can be drawn outwardly through the patient's mouth until it is no longer within tube section 14. The portion of tube section 14 positioned external to the patient is cut to an appropriate length. Measurement indicia may be provided on tube section 14 to facilitate this process. An external PEG tube retention member of known construction is placed over the remaining portion of tube section 14 and is moved into contact with the patient's skin. Endoscope 36 is then used to view the position of retaining member 34 within the stomach. Following confirmation of the position of retaining member 34, endoscope 36 is withdrawn from the patient through the patient's mouth.

The second embodiment of the method of the present invention includes the step of providing apparatus 10 having an introducer section 12 and a tube section 14. Introducer section 12 preferably is approximately 12–30 inches in length and is constructed of a material having a Shore A hardness in the range of substantially 60–90. Distal end portion 16 of introducer section 12 is introduced into the patient's mouth and advanced into the patient's stomach by pushing on introducer section 12. Following the application of a topical anesthetic to a target site on the patient's skin, an incision is made through the patient's abdominal wall into the stomach. Needle or cannula 40 is then inserted into the incision and an endoscope is inserted into the stomach through the needle 40. A grasping tool associated with the endoscope is then used to grasp graspable member 24 of apparatus 10. The grasping tool can be a part of the endoscope or can be a separate element inserted through needle 40 with the endoscope.

After grasping tool 42 has grasped graspable member 24, grasping tool 42 is pulled outwardly through the abdominal incision, thereby causing distal end portion 16 of introducer section 12 to pass outwardly through the abdominal incision. Further outward movement of grasping tool 42 and introducer section 12 is imparted until retaining member 34 of tube section 14 engages the interior wall of the patient's stomach. The portion of tube section 14 positioned external to the patient is cut to an appropriate length. Measurement indicia may be provided on tube section 14 to facilitate this process. An external PEG tube retention member of known construction is placed over the remaining portion of tube section 14 and is moved into contact with the patient's skin.

Although the apparatus and method of the present invention have been described herein with respect to certain preferred embodiments, it will be appreciated by one of ordinary skill in the art that various modifications can be made to the present invention. Such modifications are intended to be within the scope of the appended claims.

What is claimed is:

1. A method for placing a feeding tube in a patient, said method comprising:

providing a feeding tube defining a lumen therethrough, said feeding tube having a distal end portion and a proximal end portion, a first aperture defined through said feeding tube at said distal end portion of said feeding tube, a second aperture defined through said feeding tube at said proximal end portion of said feeding tube, said first and second apertures providing fluid communication between said lumen defined through said feeding tube and an external environment of said feeding tube, said feeding tube having a graspable member on said distal end portion;

providing an endoscope having a viewing portion;

inserting said viewing portion of said endoscope into said lumen defined through said feeding tube;

introducing said distal end portion of said feeding tube into a patient's mouth;

advancing said distal end portion of said feeding tube through a patient's esophagus and into a patient's stomach;

forming an incision through a patient's abdominal wall;

advancing a grasping tool through said incision formed through a patient's abdominal wall;

grasping said graspable member using said grasping tool;

withdrawing said grasping tool from a patient's stomach and advancing said distal end portion of said feeding tube outwardly from a patient's stomach through said incision; and withdrawing said endoscope from a patient's stomach by pulling said endoscope outwardly through a patient's mouth.

2. A method in accordance with claim 1, wherein said method further comprises holding said endoscope substantially stationary while advancing said feeding tube apparatus outwardly through said incision, thereby exposing said endoscope from within said feeding tube apparatus.

3. A method in accordance with claim 1, wherein said distal end portion of said feeding tube apparatus is constructed of a polyurethane material having a hardness of substantially 60–90 Shore A.

4. A method in accordance with claim 1, wherein said proximal end portion of said feeding tube apparatus is constructed of a material having a hardness of substantially 30–70 Shore A.

5. A method in accordance with claim 1, wherein said method further comprises viewing a patient's esophagus with said viewing portion of said endoscope while advancing said distal end portion of said feeding tube through a patient's esophagus and into a patient's stomach.

6. A method in accordance with claim 1, wherein said method further comprises viewing a patient's stomach with said viewing portion of said endoscope prior to withdrawing said endoscope from a patient's stomach.

7. A method in accordance with claim 1, wherein said method further comprises inserting a needle into said incision through a patient's abdominal wall prior to advancing a grasping tool through said incision formed through a patient's abdominal wall, and wherein said grasping tool is advanced into a patient's stomach through said needle.

8. A method for placing a feeding tube in a patient, said method comprising:

provinding a feeding tube apparatus comprising:

an introducer section defining a lumen therethrough, said introducer section having a proximal end portion and a distal end portion, said introducer section defining an aperture therethrough at said distal end portion thereof, a graspable member mounted on said distal end portion; and a tube section defining a lumen therethrough, said tube section having a proximal end portion and a distal end portion, said tube section defining an aperture therethrough at said proximal end portion thereof, said distal end portion of said tube section mounted on said proximal end portion of said introducer section, said lumen defined through said introducer section in fluid communication with said lumen defined through said tube section;

providing an endoscope having a viewing portion;

inserting said viewing portion of said endoscope into said aperture defined by said tube section at said proximal end portion thereof and advancing said endoscope through said lumen defined through said tube section and said lumen defined through said introducer section until said viewing portion of said endoscope is positioned proximate said aperture defined through said introducer section;

introducing said distal end portion of said introducer section of said feeding tube apparatus into a patient's mouth;

advancing said distal end portion of said introducer section of said feeding tube apparatus through a patient's esophagus and into a patient's stomach;

forming an incision through a patient's abdominal wall;

advancing a grasping tool through said incision formed through a patient's abdominal wall;

grasping said graspable member using said grasping tool;

withdrawing said grasping tool from a patient's stomach and advancing said feeding tube apparatus outwardly from a patient's stomach through said incision; and withdrawing said endoscope from a patient's stomach by pulling said endoscope outwardly through a patient's mouth.

\* \* \* \* \*